(12) United States Patent
Li

(10) Patent No.: US 11,998,392 B2
(45) Date of Patent: Jun. 4, 2024

(54) SHEAR WAVE ELASTICITY MEASUREMENT METHOD AND SHEAR WAVE ELASTICITY IMAGING SYSTEM

(71) Applicants: SHENZHEN MINDRAY BIO-MEDICAL ELECTRONICS CO., LTD., Guangdong (CN); SHENZHEN MINDRAY SCIENTIFIC CO., LTD., Guangdong (CN)

(72) Inventor: Shuangshuang Li, Shenzhen (CN)

(73) Assignees: Shenzhen Mindray Bio-Medical Electronics Co., Ltd., Shenzhen (CN); Shenzhen Mindray Scientific Co., Ltd., Shenzhen (CN)

( * ) Notice: Subject to any disclaimer, the term of this patent is extended or adjusted under 35 U.S.C. 154(b) by 645 days.

(21) Appl. No.: 17/097,881

(22) Filed: Nov. 13, 2020

(65) Prior Publication Data

US 2021/0077072 A1 Mar. 18, 2021

Related U.S. Application Data

(63) Continuation of application No. PCT/CN2018/086840, filed on May 15, 2018.

(51) Int. Cl.
*A61B 8/08* (2006.01)
*A61B 8/00* (2006.01)
*G01N 29/04* (2006.01)

(52) U.S. Cl.
CPC .............. *A61B 8/485* (2013.01); *A61B 8/463* (2013.01); *A61B 8/469* (2013.01); *A61B 8/5223* (2013.01);

(Continued)

(58) Field of Classification Search
CPC .......... A61B 8/485; A61B 8/463; A61B 8/469; A61B 8/5223; A61B 8/54; A61B 8/5207;
(Continued)

(56) References Cited

U.S. PATENT DOCUMENTS 6,508,768 B1 * 1/2003 Hall .................... G01S 7/52061
600/443
6,558,324 B1 * 5/2003 Von Behren ........ G01S 7/52074
600/443

(Continued)

FOREIGN PATENT DOCUMENTS

CN 104203112 A 12/2014
CN 104605891 A 5/2015
(Continued)

OTHER PUBLICATIONS

PCT International Preliminary Report on Patentability dated Nov. 26, 2020, issued in related International Application No. PCT/CN2018/086840, with English translation (10 pages).

(Continued)

*Primary Examiner* — Sanjay Cattungal
(74) *Attorney, Agent, or Firm* — Sheppard Mullin Richter & Hampton LLP

(57) ABSTRACT

A shear wave elasticity measurement method and a shear wave elasticity imaging system are disclosed. For each pair of corresponding shear waves, an echo signal within a continuous period of time can be obtained only at a third position, so that an elasticity parameter corresponding to the target area can be obtained according to the echo signal within the continuous period of time. Not only the position required for obtaining an echo signal is few, but also the total data volume required for obtaining the echo signal is few. The calculation method is also easy, which significantly reduces the system performance requirement.

18 Claims, 3 Drawing Sheets

(52) U.S. Cl.
CPC .............. *A61B 8/54* (2013.01); *G01N 29/043* (2013.01); *G01N 2291/02827* (2013.01)

(58) Field of Classification Search
CPC ....... G01N 29/043; G01N 2291/02827; G01N 2291/011; G01N 2291/0422; G01N 29/0654; G01S 7/52022; G01S 7/52042; G01S 7/52085
See application file for complete search history.

(56) References Cited

U.S. PATENT DOCUMENTS

| | | | |
|---|---|---|---|
| 8,469,891 B2* | 6/2013 | Maleke | A61B 5/055 73/602 |
| 9,066,679 B2* | 6/2015 | Beach | A61B 8/08 |
| 9,603,583 B2* | 3/2017 | Choi | A61B 8/485 |
| 9,726,647 B2* | 8/2017 | Walker | G01N 29/4436 |
| 10,342,514 B2* | 7/2019 | Kanayama | A61B 8/5207 |
| 10,959,703 B2 | 3/2021 | Hollender et al. | |
| 2009/0056453 A1* | 3/2009 | McAleavey | A61B 8/485 73/597 |
| 2009/0270730 A1* | 10/2009 | Azuma | A61B 8/485 600/443 |
| 2009/0292205 A1* | 11/2009 | Osaka | G01S 7/52042 600/443 |
| 2009/0304246 A1* | 12/2009 | Walker | G01S 15/8979 382/128 |
| 2011/0263978 A1* | 10/2011 | Chen | A61B 8/485 600/438 |
| 2013/0102932 A1* | 4/2013 | Cain | A61N 7/02 601/2 |
| 2013/0211253 A1* | 8/2013 | Hsu | A61B 8/485 600/438 |
| 2013/0218012 A1* | 8/2013 | Specht | G01S 15/8929 367/7 |
| 2014/0064021 A1* | 3/2014 | Nagae | G01S 7/52047 367/7 |
| 2014/0064022 A1* | 3/2014 | Nagae | G01S 7/52046 367/7 |
| 2014/0064023 A1* | 3/2014 | Nagae | G01S 7/52063 367/7 |
| 2014/0276058 A1* | 9/2014 | Fan | A61B 5/4872 600/442 |
| 2014/0330122 A1* | 11/2014 | Baghani | A61B 8/463 600/438 |
| 2015/0119712 A1 | 4/2015 | Tanigawa | |
| 2015/0133783 A1* | 5/2015 | Tabaru | A61B 8/485 600/438 |
| 2015/0148673 A1* | 5/2015 | Yoshikawa | A61B 8/5207 600/438 |
| 2015/0164476 A1* | 6/2015 | Kong | G01S 7/52022 600/438 |
| 2015/0182122 A1* | 7/2015 | Bamber | G01S 7/52022 600/407 |
| 2015/0192547 A1* | 7/2015 | Lee | A61B 8/06 73/641 |
| 2015/0272547 A1* | 10/2015 | Freiburger | A61B 8/52 600/438 |
| 2015/0320394 A1* | 11/2015 | Arnal | A61B 8/485 600/438 |
| 2015/0342566 A1 | 12/2015 | Matsumoto et al. | |
| 2016/0089113 A1* | 3/2016 | Choi | G01S 15/892 600/438 |
| 2016/0128674 A1* | 5/2016 | Shin | G01S 7/52071 600/436 |
| 2016/0327525 A1* | 11/2016 | Li | A61B 8/485 |
| 2017/0042511 A1 | 2/2017 | Labyed et al. | |
| 2017/0112471 A1* | 4/2017 | Toji | A61B 8/4254 |
| 2017/0333004 A1 | 11/2017 | Yoshikawa | |
| 2017/0340310 A1* | 11/2017 | Carlini | G01S 7/52022 |
| 2017/0347990 A1* | 12/2017 | Watanabe | G01S 7/52022 |
| 2017/0360408 A1* | 12/2017 | Toji | G01S 7/52017 |
| 2018/0296190 A1* | 10/2018 | Susumu | A61B 8/5269 |
| 2019/0046160 A1 | 2/2019 | Li et al. | |
| 2019/0183461 A1* | 6/2019 | Sonoyama | G01S 7/52042 |
| 2019/0254629 A1 | 8/2019 | Li et al. | |
| 2020/0060654 A1* | 2/2020 | Nguyen | G01S 7/52042 |
| 2023/0044531 A1* | 2/2023 | Etaix | G01N 29/07 |

FOREIGN PATENT DOCUMENTS

| | | |
|---|---|---|
| CN | 106419961 A | 2/2017 |
| CN | 106456108 A | 2/2017 |
| CN | 106999162 A | 8/2017 |
| CN | 107708575 A | 2/2018 |
| WO | 2018/023336 A1 | 2/2018 |

OTHER PUBLICATIONS

First Search dated Mar. 3, 2022, issued in related Chinese Application No. 201880056527.2 (3 pages).
First Office Action dated Mar. 9, 2022, issued in related Chinese Application No. 201880056527.2, with English machine translation (25 pages).
PCT International Search Report and the Written Opinion dated Jan. 24, 2019, issued in related International Application No. PCT/CN2018/086840, with partial English translation (8 pages).

* cited by examiner (a)

(b)

SHEAR WAVE ELASTICITY MEASUREMENT METHOD AND SHEAR WAVE ELASTICITY IMAGING SYSTEM

CROSS-REFERENCE TO RELATED APPLICATION

This application is a continuation application of International Patent Application No. PCT/CN2018/086840, filed with the China National Intellectual Property Administration (CNIPA) of People's Republic of China on May 15, 2018, and entitled "SHEAR WAVE ELASTICITY MEASUREMENT METHOD AND SHEAR WAVE ELASTOGRAPHY SYSTEM". The entire content of the above-identified application is incorporated herein by reference.

TECHNICAL FIELD

The present disclosure relates to shear wave elasticity measurement methods and shear wave elasticity imaging systems.

BACKGROUND

Medical ultrasound elasticity imaging mainly refers to a series of imaging and signal processing techniques for the purpose of detecting the difference in tissue elasticity. The obtained tissue elasticity difference (or softness and hardness) information may be used for auxiliary detection, benign and malignant discrimination and prognosis recovery evaluation, etc. of the cancer lesions.

The current medical ultrasound elasticity imaging technologies mainly include pressure elasticity imaging and Shear Wave Elasticity imaging (SWE).

The pressure elasticity imaging has been developed for the longest time and the technology is the most mature, but it has higher requirement for the operator's technique. In the pressure elasticity imaging, a certain deformation may be generated by pressing the tissue with the probe. The probe may transmit the ultrasound waves and receive the echo signals, and calculate and image the strain, strain rate or other parameters related to the elasticity of the tissue, thereby representing the difference in elasticity between different tissues. Since the strain parameter such as the strain or the strain rate is very sensitive to pressure, the pressure applied to the tissue through the probe in the pressure elasticity imaging technology needs to be as uniform and stable as possible, which will lead to higher requirement for the operator's technique. In addition, because the pressures applied to the tissue by the operator through the probe in different times of imaging are difficult to keep consistent, it is difficult to ensure the repeatability and stability of the imaging.

In the shear wave elasticity imaging, a shear wave may be generated inside the tissue and the propagation parameter (such as the propagation velocity) of the shear wave may be detected. Since the elasticity (or hardness) of the tissue will affect the propagation parameter of the shear wave, the propagation parameter of the shear wave can represent the elasticity difference (or the degree of softness) of the tissue, that is, the detected propagation parameter may be used for elasticity imaging. Because it no longer relies on the operator to apply a specific pressure to the tissue as the pressure elasticity imaging, the shear wave elasticity imaging has made great progress in stability and repeatability. However, because the propagation parameter of the shear wave will be detected or calculated, the shear wave elasticity imaging systems often have complex detection or calculation methods, and the amount of data that needs to be processed is also large, which requires high system performance.

SUMMARY

In one embodiment, a shear wave elasticity measurement method is provided, which may include: generating a first shear wave at a first position on a boundary of a target area; generating a second shear wave at a second position on the boundary of the target area, where the second position is located on a propagation path of the first shear wave; transmitting an ultrasound wave to a third position to detect the first shear wave and the second shear wave and receiving echoes of the ultrasound wave to obtain an echo signal, where the third position is located outside the target area and the first shear wave propagates to the third position through the second position; obtaining a time when the first shear wave reaches the third position and a time when the second shear wave reaches the third position according to the echo signal; and calculating an elasticity parameter of the target area according to the time when the first shear wave reaches the third position, the time when the second shear wave reaches the third position and a distance between the first position and the second position.

In one embodiment, a shear wave elasticity imaging system is provided, which may include: a probe; a transmitting controller configured to control the probe to generate a first shear wave at a first position on a boundary of a target area, control the probe to generate a second shear wave at a second position on the boundary of the target area, and control the probe to transmit an ultrasound wave to a third position to detect the first shear wave and the second shear wave, where, the second position is located on a propagation path of the first shear wave, and the third position is located outside the target area and the first shear wave propagates to the third position through the second position; a receiving controller configured to control the probe to receive echoes of the ultrasound wave transmitted to the third position to obtain an echo signal; and an image processor configured to obtain a time when the first shear wave reaches the third position and a time when the second shear wave reaches the third position according to the echo signal, and calculate an elasticity parameter of the target area according to the time when the first shear wave reaches the third position, the time when the second shear wave reaches the third position and a distance between the first position and the second position.

In one embodiment, a shear wave elasticity measurement method is provided, which may include: generating a first shear wave at a first position on a boundary of a target area; generating a second shear wave at a second position on the boundary of the target area, where the second position is located on a propagation path of the first shear wave; transmitting an ultrasound wave to a third position to detect the first shear wave and the second shear wave passing through the third position and receiving echoes of the ultrasound wave to obtain an echo signal that contains an information of the first shear wave and the second shear wave passing through the third position, where the third position is located outside the target area and the first shear wave propagates to the third position through the second position; and obtaining an elasticity parameter of the target area according to the echo signal.

In one embodiment, a shear wave elasticity imaging system is provided, which may include: a probe; a transmitting controller configured to control the probe to generate a first shear wave at a first position on a boundary of a target area, control the probe to generate a second shear wave at a second position on the boundary of the target area, and control the probe to transmit an ultrasound wave to a third position to detect the first shear wave and the second shear wave passing through the third position, where, the second position is located on a propagation path of the first shear wave, and the third position is located outside the target area and the first shear wave propagates to the third position through the second position; a receiving controller configured to control the probe to receive echoes of the ultrasound wave transmitted to the third position to obtain an echo signal that contains an information of the first shear wave and the second shear wave passing through the third position; and an image processor configured to obtain an elasticity parameter of the target area according to the echo signal.

In the shear wave elasticity measurement methods and the shear wave elasticity imaging systems above, since for each pair of shear waves, the elasticity parameter of the target area may be obtained according to the echo signals in a continuous period of time obtained only at the third position, not only the number of the positions where it is desired to obtain the echo signals is reduced, but also the total amount of the echo signals that are desired to be obtained is decreased, and the calculation method is also simple, which greatly reduces the performance requirement to the system.

DETAILED DESCRIPTION

Medical ultrasound elasticity imaging may refer to a series of imaging and signal processing technologies for the purpose of representing the difference in tissue elasticity. In the present embodiments, the shear wave may be generated in the tissue, the ultrasound waves may be transmitted to detect the propagation of the shear wave in the tissue, and the elasticity parameter may be calculated according to the received echo signals.

Figure 1:
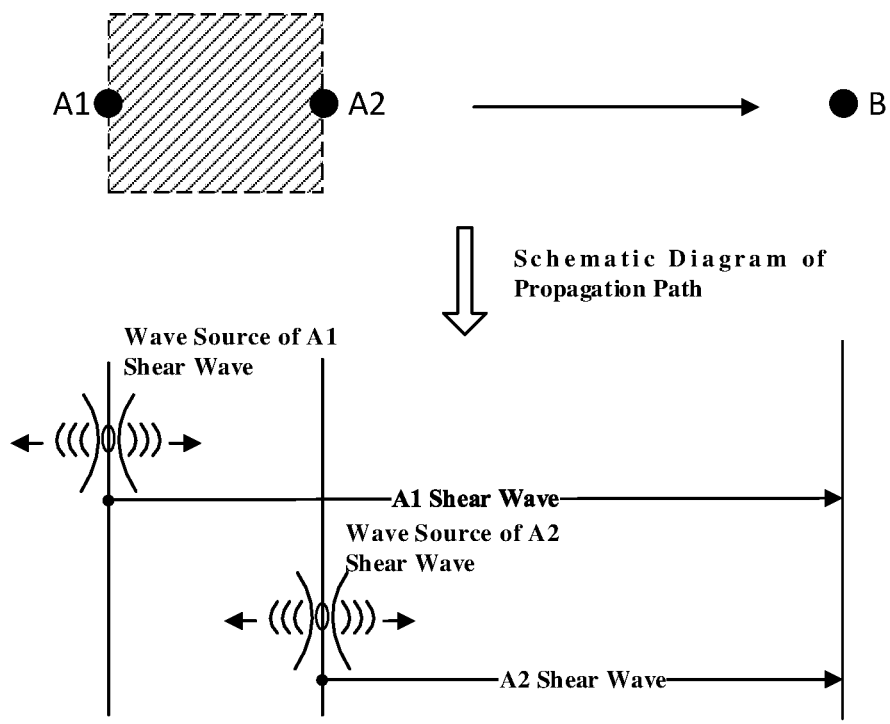
FIG. 1 is a schematic diagram of the propagation paths of two shear waves generated in the target area in one embodiment.

Referring to FIG. 1, the target tissue desired to be examined (that is, the elasticity or softness, etc. of this part of the tissue is desired to be known) may be represented with the area filled with slashes, which may be referred to as the target area. The target area may be selected by the user on the ultrasound image. Alternatively, the target area may be an image area of a certain tissue automatically recognized by the system. The shape of the target area may not be limited to the rectangle in FIG. 1, but may also be a square or other regular or irregular shape.

The shear waves may be respectively generated at the target point A1 (an example of the first position below) and the target point A2 (an example of the second position below) on the boundary of the target area. At a position B (an example of the third position below) outside the target area, the two shear waves passing through the position B may be detected by transmitting the ultrasound wave to the position B through the probe to obtain the echo signals. The echo signals contain the information of the two shear waves passing through the position B. In the above process, the shear wave generated at A1 will propagate to the position B through A2, and the shear wave generated at A2 will also propagate to the position B. For the sake of simplicity of description, the shear wave generated at A1 may be referred to as A1 shear wave (first shear wave), and the shear wave generated at A2 may be referred to as A2 shear wave (second shear wave). In the present disclosure, the shear wave may be generated by the acoustic radiation force of the focused ultrasound beams transmitted into the tissue through the probe.

When the A1 shear wave reaches the observation point B, the propagation path thereof in the tissue is A1→A2→B. When the A2 shear wave reaches the observation point B, the propagation path thereof in the tissue is A2→B. In the simplest case that the A1 shear wave and the A2 shear wave are generated at the same time, that is, the A1 shear wave and the A2 shear wave start to propagate to the point B at the same time, the two shear waves will arrive at the point B one after the other, that is, there will be a time difference Δt between the times when the two shear waves arrive at the point B. The reason is that the A1 shear wave will propagate additional distance A1→A2 in order to reach the point B compared with the A2 shear wave (because both the A1 shear wave and the A2 shear wave pass through the same path A2→B, the times spent in this path are the same). In other words, it takes time Δt for the shear wave to propagate in the path A1→A2. Therefore, when the distance between A1 and A2 and the time difference Δt are known, the average velocity of the shear wave in the target area may be calculated by dividing the distance between A1 and A2 by the time difference Δt.

The distance between A1 and A2 may be obtained by real-time measurement, or may be a preset value.

Figure 2:
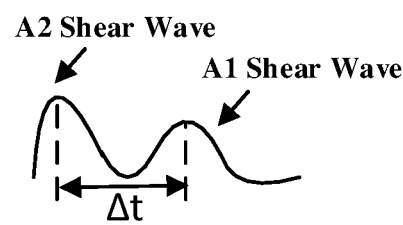
FIG. 2 is a typical curve of the displacement of the tissue at point B over the time obtained by receiving the echo signals of the two shear waves in FIG. 1 at the point B in one embodiment.

The time difference Δt between the times when the A1 shear wave and the A2 shear wave reach the point B may be obtained according to the echo signals received at the point B. Referring to FIG. 2 that is a typical curve of the displacement of the tissue at point B over the time obtained by receiving the echo signals of the two shear waves at the point B, since the A2 shear wave reaches the observation point B only through the path A2→B while the A1 shear wave reaches the observation point B through the path A1→A2 and the path A2→B, the A2 shear wave will reach the point B with a shorter time and a small attenuation. Therefore, according to the time or the peak amplitude, it may be determined that the first peak in the figure indicates the arriving of the A2 shear wave at the point B and the second peak indicates the arriving of the A1 shear wave at the point B. The time difference Δt between the two peaks is the time difference Δt between the times when the A1 shear wave and the A2 shear wave arrive at the point B.

The case that the A1 shear wave and the A2 shear wave are generated at the same time has been discussed above. In another case, the A1 shear wave and the A2 shear wave may be generated one after another. Specifically, the A1 shear wave may be generated before the A2 shear wave, or after the A2 shear wave. In this case, the concept and principle for calculating the average velocity of the shear wave in the target area may be similar, except that the way for obtaining the times spent by the A1 shear wave and A2 shear wave for reaching the position where the echo signals are received are slightly different. For example, the time t1 when the A1 shear wave is generated and the time t2 when the A2 shear wave is generated may be obtained, and, according to the curve of the displacement of the tissue at the point B over time obtained according to the echo signals received at the point B, the time t3 when the A1 shear wave reaches the point B (that is, the time corresponding to the smaller peak in the curve) and the time t4 when the A2 shear wave reaches the point B (that is, the time corresponding to the larger peak in the curve) may be obtained. Therefore, the time spent by the A1 shear wave to reach the point B is t3−t1, and the time spent by the A2 shear wave to reach the point B is t4−t2. In the case shown in FIG. 1, since the point B is closer to A2, the time t3−t1 is greater than the time t4−t2. Therefore, the time difference Δt between the times spent by the A1 and A2 shear waves to reach the position where the echo signals are received is (t3−t1)−(t4−t2).

After the average velocity of the shear wave in the target area is obtained, other elasticity related parameter may be calculated, such as the Young's modulus or the shear modulus. For an isotropic elastomer, there is an approximate relationship between the propagation velocity of the shear wave and the elastic modulus as follows:

$$E = 3\rho c^2 = 3G$$

In the formula, E represents the Young's modulus of the tissue, G represents the shear modulus of the tissue, c represents the velocity of the shear wave, and ρ represents the tissue density. The greater the Young's modulus, the greater the hardness of the tissue.

The concepts and principles of the present disclosure have been described above. In the following, the present disclosure will be further illustrated with reference to several embodiments.

Figure 3:
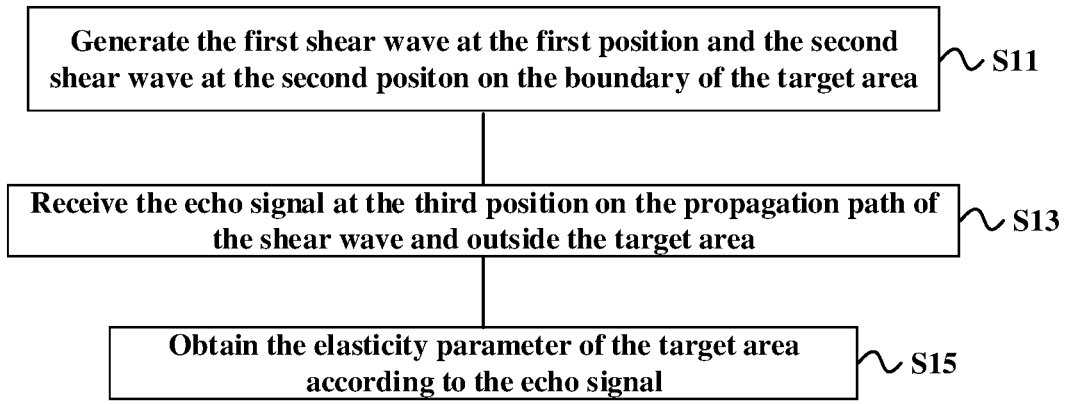
FIG. 3 is a schematic flowchart of a shear wave elasticity measurement method in one embodiment.

Referring to FIG. 3, in one embodiment, a shear wave elasticity measurement method is provided, which may include steps S11 to S15.

Figure 4:
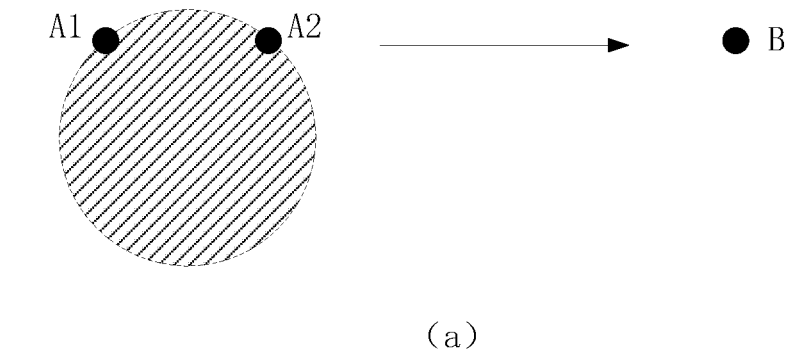
FIG. 4(a) and FIG. 4(b) are schematic diagrams of selecting different positions on the boundary of the target area as the shear wave generating positions in one embodiment.
Figure 4:
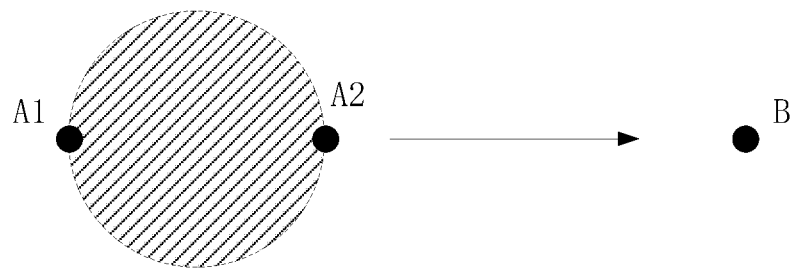

In step S11, the first shear wave may be generated at the first position on the boundary of the target area, and the second shear wave may be generated at the second position on the boundary of the target area. The second position may be located on the propagation path of the first shear wave. In one embodiment, the second position may be different from the first position. In step S11, the first shear wave may be one group of shear waves, and the second shear wave may also be one group of shear waves. In the two groups of shear waves, each group of shear waves may include at least one shear wave, and for each shear wave in one group of shear waves, there may be one corresponding shear wave in the other group of shear waves. For the two corresponding shear waves, the wave source of one shear wave may be located on the propagation path of the other shear wave. In step S11, the first position and the second position may be selected on the boundary of the target area in many ways so as to generate the shear waves, such as shown in FIG. 4(a) and FIG. (b). When the generated shear wave propagates through more tissues in the target area, the echo signals obtained by tracking the shear wave with the ultrasound waves at the third position (detailed below) will contain more information of the tissue in the target area, and the calculated elasticity parameter of the target area will more accurate. For example, when calculating the elasticity parameter of the target area, generating the shear waves at the two positions A1 and A2 shown in FIG. 4(b) may be better than at the two positions shown in FIG. 4(a). Therefore, in one embodiment, in step S11, the group of shear waves may be respectively generated at two positions with the largest distance on the boundary of the target area, that is, the selected first position and second position on the boundary of the target area may have the maximum distance therebetween.

In one embodiment, the first position may include one target point, and the second position may also include one target point. Accordingly, the first shear wave may include one shear wave at the target point at the first position, and the second shear wave may include one shear wave at the target point at the second position. In another embodiment, the first position may include multiple target points, and the second position may also include multiple target points. Correspondingly, the first shear wave may include multiple shear waves at the multiple target points at the first position, and the second shear wave may include multiple shear waves at the multiple target points at the second position. The multiple first shear waves may respectively propagate through the multiple target points at the second position to the third position. In this case, the third position may include multiple detection points, and each detection point may correspond to one pair of first shear wave and second shear wave that correspond to each other. In each pair of shear waves, the first shear wave may propagate through the target point corresponding to the corresponding second shear wave at the second position to the detection point corresponding to said pair of shear waves. Correspondingly, in step S13 described below, the probe may transmit the ultrasound waves to such detection point and receive the ultrasound echoes to detect the pair of shear waves passing through such detection point.

In one embodiment, when the first position includes multiple target points, the multiple target points may be arranged in a straight line or other shape. When the second position includes multiple target points, the multiple target points may also be arranged in a straight line or other shape.

In step S11, as described above, the first shear wave and the second shear wave may be generated by the acoustic radiation force of the focused ultrasound beams transmitted by the probe into the tissue.

In one embodiment, the first shear wave and the second shear wave may be generated at the same time, so that the subsequent calculation may be relatively simple. Alternatively, the first shear wave and the second shear wave may be generated at different times.

In step S13, the ultrasound waves may be transmitted to the third position to detect each pair of first shear waves and second shear waves, and the echoes of the ultrasound waves may be received to obtain the echo signals. Here, the third position may be located outside the target area, and the first shear wave propagates to the third position through the second position. The echo signals contain the information of the first shear wave and the second shear wave passing through the third position, such as the information related to the time when the first shear wave passes through the third position and information related to the time when the second shear wave passes through the third position.

In step S15, for each pair of corresponding shear waves, the elasticity parameter of the target area may be obtained according to the echo signals obtained in step S13.

For example, in one embodiment, the step S15 may include: obtaining the time when the first shear wave reaches the third position and the time when the second shear wave reaches the third position according to the echo signals, and calculating the elasticity parameter of the target area according to the time when the first shear wave reaches the third position, the time when the second shear wave reaches the third position and the distance between the first position and the second position. For example, according to the time when the first shear wave reaches the third position and the time when the second shear wave reaches the third position, the time difference between the times when such pair of shear waves reach the third position may be obtained, and based on this time difference and the distance between the first position and the second position, the elasticity parameter of the target area may be obtained. In one embodiment, the curve of the echo signal over time may be obtained. According to the curve, the peaks of the curve may indicate the times when the two corresponding shear waves respectively reach the third position, and the time interval between two adjacent peaks may be the time difference between the times when the two shear waves reach the third position.

In one embodiment, in the case that the first position and the second position respectively include multiple target points, in other words, multiple pairs of shear waves are generated in step S11, the elasticity parameter of the target area may be calculated based on each pair of shear waves. Thereafter, these elasticity parameters may be averaged to obtain the average elasticity parameter of the target area that can more accurately represent the elasticity of the target area. In one embodiment, the elasticity parameter may include one or more of the average velocity of the shear wave, the Young's modulus, and the shear modulus, or other elasticity parameters.

The shear wave elasticity measurement methods have been described above. In order to increase the ease of use, in one embodiment, the shear wave elasticity measurement method may further include: transmitting the ultrasound beams to the target area; receiving the ultrasound echoes from the target area to obtain the echo signals for generating the ultrasound image; generating the ultrasound image according to the echo signals and displaying the ultrasound image; obtaining the selection instruction of the user for selecting the target area on the ultrasound image; and determining the first position and the second position according to the selection instruction. In one embodiment, the elasticity parameter may be displayed on the ultrasound image. The elasticity parameter may be displayed in the form of text or icons, and when the target area changes, the displayed elasticity parameter may be updated accordingly.

Figure 5:
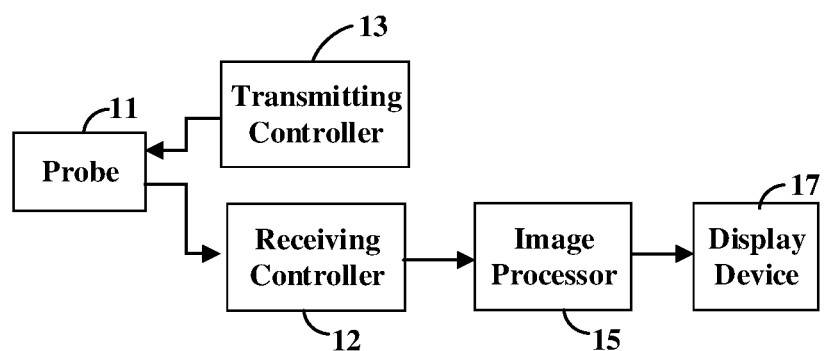
FIG. 5 is a schematic block diagram of a shear wave elasticity imaging system in one embodiment.

Referring to FIG. 5, a shear wave elasticity imaging system may also be provided. In one embodiment, the shear wave elasticity imaging system may include a probe 11, a transmitting controller 13, a receiving controller 12 and an image processor 15. In one embodiment, the shear wave elasticity imaging system may further include a display device 17.

The probe 11 may include a piezoelectric element array. The probe 11 may transmit the focused ultrasound waves into the tissue to generate the shear wave at a certain position in the tissue, and may transmit the ultrasound waves to a certain position in the tissue to track or detect the propagation of the shear wave.

The transmitting controller 13 may control the shear wave generation timing and the transmitting and receiving timing of the ultrasound beams. Specifically, the transmitting controller 13 may control the probe 11 to transmit the focused ultrasound waves to the first position on the boundary of the target area so as to generate the first shear wave at the first position on the boundary of the target area through the acoustic radiation force of the focused ultrasound waves. The transmitting controller 13 may also control the probe 11 to transmit the focused ultrasound waves to the second position on the boundary of the target area so as to generate the second shear wave at the second position on the boundary of the target area through the acoustic radiation force of the focused ultrasound waves. Here, the second position may be located on the propagation path of the first shear wave.

Here, the first shear wave may be a group of shear waves, and the second shear wave may also be a group of shear waves. Each group of shear waves may include at least one shear wave, and for each shear wave in one group of shear waves, there may be a corresponding shear wave in the other group of shear waves. In the two corresponding shear waves, the wave source of one shear wave may be located on the propagation path of the other shear wave.

For each pair of shear waves, the transmitting controller 13 may control the probe 11 to transmit the ultrasound waves to the third position to detect such pair of first and second shear waves. The receiving controller 12 may control the probe to receive the echoes of the ultrasound waves to obtain the echo signals. Here, the third position may be located outside the target area and the first shear wave may propagate to the third position through the second position. The echo signals contain the information of the first shear wave and the second shear wave passing through the third position, such as the information related to the time when the first shear wave passes through the third position and the information related to the time when the second shear wave passes through the third position.

In one embodiment, the transmitting controller 13 may control the probe 11 to generate the second shear wave at the second position different from the first position. In one embodiment, the first position and the second position may have the maximum distance therebetween on the boundary of the target area.

In one embodiment, the first position may include one target point, and the second position may also include one target point. Accordingly, the first shear wave may include one shear wave at the target point at the first position, and the second shear wave may include one shear wave at the target point at the second position. In another embodiment, the first position may include multiple target points, and the second position may also include multiple target points. Correspondingly, the first shear wave may include multiple shear waves at the multiple target points at the first position, and the second shear wave may include multiple shear waves at the multiple target points at the second position. The multiple first shear waves may respectively propagate through the multiple target points at the second position to the third position. In this case, the third position may include multiple detection points, and each detection point may correspond to one pair of first shear wave and second shear wave that correspond to each other. In each pair of shear waves, the first shear wave may propagate through the target point corresponding to the corresponding second shear wave at the second position to the detection point corresponding to said pair of shear waves. Correspondingly, the transmitting controller 13 may control the probe 11 to transmit the ultrasound waves to such detection point to detect said pair of shear waves passing through said detect point. The receiving controller 12 may control the probe 11 to receive the ultrasound echoes to obtain the echo signals. The echo signals contain the information of the first shear wave and the second shear wave passing through the detection point.

In one embodiment, when the first position includes multiple target points, the multiple target points may be arranged in a straight line or other shape. When the second position includes multiple target points, the multiple target points may also be arranged in a straight line or other shape.

As described above, the first shear wave and the second shear wave may be generated by the acoustic radiation force of the focused ultrasound beams transmitted by the probe into the tissue under the control of the transmitting controller 13.

In one embodiment, the transmitting controller 13 may control the probe 11 to simultaneously generate the first shear wave and the second shear wave, so that the subsequent calculation may be relatively simple. Alternatively, the transmitting controller 13 may control the probe 11 to generate the first shear wave and the second shear wave at different times.

The image processor 15 may calculate the elasticity parameter of the target area according to the obtained echo signals for each pair of shear waves.

In one embodiment, the elasticity parameter obtained by the image processor 15 may include one or more of the average velocity of the shear wave, the Young's modulus and the shear modulus, or other elasticity parameters.

In one embodiment, the image processor may obtain the time when the first shear wave reaches the third position and the time when the second shear wave reaches the third position according to the echo signals, and calculate the elasticity parameter of the target area according to the time when the first shear wave reaches the third position, the time when the second shear wave reaches the third position and the distance between the first position and the second position. For example, according to the time when the first shear wave reaches the third position and the time when the second shear wave reaches the third position, the time difference between the times when such pair of shear waves reach the third position may be obtained, and based on this time difference and the distance between the first position and the second position, the elasticity parameter of the target area may be obtained. In one embodiment, the curve of the echo signal over time may be obtained. According to the curve, the peaks of the curve may indicate the times when the two corresponding shear waves respectively reach the third position, and the time interval between two adjacent peaks may be the time difference between the times when the two shear waves reach the third position.

The display device 17 may display the elasticity parameter. In one embodiment, the transmitting controller 13 may control the probe 11 to transmit the ultrasound beams to the target area, and the receiving controller 12 may control the probe 11 to receive the ultrasound echoes of the ultrasound beams from the target area to obtain the echo signals for generating the ultrasound image. The image processor 15 may obtain the ultrasound image of the target area according to the echo signals for generating the ultrasound image. The ultrasound image may be displayed on the display device 17, and the elasticity parameter may be displayed on the ultrasound image. In one embodiment, the display device 17 may display the elasticity parameter in a text or icon, and when the target area changes, the displayed elasticity parameter may be updated accordingly.

Figure 6:
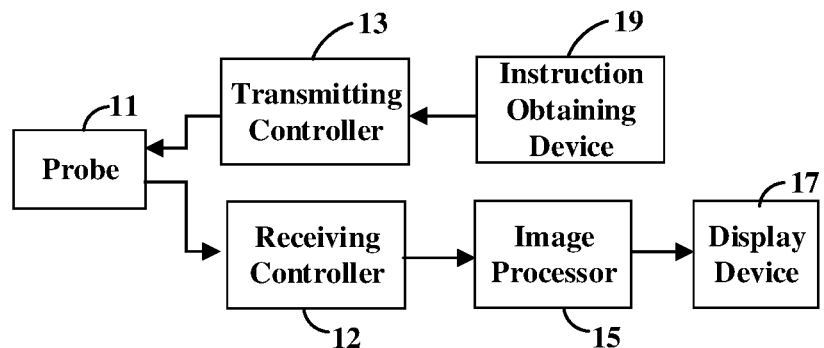
FIG. 6 is a schematic block diagram of a shear wave elasticity imaging system in one embodiment.

In order to improve the ease of use of the shear wave elasticity imaging system, referring to FIG. 6, in one embodiment, the shear wave elasticity imaging system may further include an instruction obtaining device 19 that may be configured to obtain the selection instruction of the user for selecting the target area on the ultrasound image and determine the first position and second position according to the selection instruction. The transmitting controller 13 may control the probe 11 to transmit the focused ultrasound beams to the determined first position and second position so as to generate the first shear wave and the second shear wave at the first position and the second position, respectively.

In the shear wave elasticity measurement methods and the shear wave elasticity imaging systems above, since for each pair of shear waves, the elasticity parameter of the target area may be obtained according to the echo signals in a continuous period of time obtained only at the third position, not only the number of the positions where it is desired to obtain the echo signals is reduced, but also the total amount of the echo signals that are desired to be obtained is decreased, and the calculation method is also simple, which greatly reduces the performance requirement to the system.

This disclosure has been made with reference to various exemplary embodiments. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

Additionally, as will be appreciated by one of ordinary skill in the art, principles of the present disclosure may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the invention. The scope of the present invention should, therefore, be determined by the following claims.

The invention claimed is:

1. A shear wave elasticity measurement method, comprising:
    generating a first shear wave at a first position on a boundary of a target area;
    generating a second shear wave at a second position on the boundary of the target area, wherein the second position is located on a propagation path of the first shear wave;
    transmitting an ultrasound wave to a third position to detect the first shear wave and the second shear wave, and receiving echoes of the ultrasound wave to obtain an echo signal, wherein the third position is located outside the target area and the first shear wave propagates to the third position through the second position;
    obtaining a first time when the first shear wave reaches the third position and a second time when the second shear wave reaches the third position according to the echo signal; and
    calculating an elasticity parameter of the target area according to a time difference between the first time when the first shear wave reaches the third position and the second time when the second shear wave reaches the third position, and a distance between the first position and the second position.

2. The shear wave elasticity measurement method of claim 1, wherein the second position is different from the first position.

3. The shear wave elasticity measurement method of claim 2, wherein the distance between the first position and the second position is maximum on the boundary of the target area.

4. The shear wave elasticity measurement method of claim 1, wherein generating the first shear wave at the first position on the boundary of the target area comprises:
    generating multiple first shear waves at multiple target points at the first position.

5. The shear wave elasticity measurement method of claim 4, wherein generating the second shear wave at the second position on the boundary of the target area comprises:
    generating multiple second shear waves at multiple target points at the second position, wherein the multiple first shear waves respectively propagate to the third position through the multiple target points at the second position.

6. The shear wave elasticity measurement method of claim 1, wherein the first shear wave and the second shear wave are generated at a same time or at different times.

7. The shear wave elasticity measurement method of claim 1, wherein the elasticity parameter comprises one or more of an average velocity of shear wave, a Young's modulus, and a shear modulus.

8. The shear wave elasticity measurement method of claim 1, further comprising:
    transmitting an ultrasound wave to the target area and receiving ultrasound echoes from the target area to obtain an echo signal for generating an ultrasound image;
    generating an ultrasound image of the target area according to the echo signal for generating an ultrasound image;
    displaying the ultrasound image; and
    displaying the elasticity parameter.

9. The shear wave elasticity measurement method of claim 8, further comprising:
    obtaining the target area selected by a user on the ultrasound image; and
    determining the first position and the second position according to the selected target area.

10. A shear wave elasticity imaging system, comprising:
    a probe;
    a transmitting controller configured to control the probe to generate a first shear wave at a first position on a boundary of a target area, control the probe to generate a second shear wave at a second position on the boundary of the target area, and control the probe to transmit an ultrasound wave to a third position to detect the first shear wave and the second shear wave, wherein, the second position is located on a propagation path of the first shear wave, and the third position is located outside the target area and the first shear wave propagates to the third position through the second position;
    a receiving controller configured to control the probe to receive echoes of the ultrasound wave transmitted to the third position to obtain an echo signal; and
    an image processor configured to obtain a first time when the first shear wave reaches the third position and a second time when the second shear wave reaches the third position according to the echo signal, and calculate an elasticity parameter of the target area according to a time difference between the first time when the first shear wave reaches the third position and the second time when the second shear wave reaches the third position, and a distance between the first position and the second position.

11. The shear wave elasticity imaging system of claim 10, wherein the second position is different from the first position.

12. The shear wave elasticity imaging system of claim 11, wherein the distance between the first position and the second position is maximum on the boundary of the target area.

13. The shear wave elasticity imaging system of claim 10, wherein the transmitting controller is configured to control the probe to generate multiple first shear waves at multiple target points at the first position.

14. The shear wave elasticity imaging system of claim 13, wherein the transmitting controller is configured to control the probe to generate multiple second shear waves at multiple target points at the second position, wherein the multiple first shear waves respectively propagate to the third position through the multiple target points at the second position.

15. The shear wave elasticity imaging system of claim 10, wherein the transmitting controller is configured to control the probe to generate the first shear wave and the second shear wave at a same time or at different times.

16. The shear wave elasticity imaging system of claim 10, wherein the elasticity parameter obtained by the image processor comprises one or more of an average velocity of shear wave, a Young's modulus, and a shear modulus.

17. The shear wave elasticity imaging system of claim 10, further comprising a display, wherein:

the transmitting controller is further configured to control the probe to transmit an ultrasound wave to the target area, and the receiving controller is further configured to control the probe to receive ultrasound echoes from the target area to obtain an echo signal for generating an ultrasound image;

the image processor is further configured to generate an ultrasound image of the target area according to the echo signal for generating an ultrasound image; and the display is further configured to display the ultrasound image and the elasticity parameter.

18. The shear wave elasticity imaging system of claim 17, wherein the image processor is further configured to obtain a selection instruction of a user for selecting the target area on the ultrasound image and determine the first position and the second position according to the selected target area.

* * * * *